(12) United States Patent
Bäumer et al.

(10) Patent No.: US 12,228,721 B2
(45) Date of Patent: Feb. 18, 2025

(54) METHOD FOR ADJUSTING AND/OR CALIBRATING A MEDICAL MICROSCOPE AND MEDICAL MICROSCOPE

(71) Applicant: Carl Zeiss Meditec AG, Jena (DE)

(72) Inventors: Richard Bäumer, Schorndorf (DE); Marco Woerner, Gerstetten (DE)

(73) Assignee: CARL ZEISS MEDITEC AG, Jena (DE)

( * ) Notice: Subject to any disclaimer, the term of this patent is extended or adjusted under 35 U.S.C. 154(b) by 72 days.

(21) Appl. No.: 18/100,894

(22) Filed: Jan. 24, 2023

(65) Prior Publication Data
US 2023/0236407 A1    Jul. 27, 2023

(30) Foreign Application Priority Data
Jan. 25, 2022   (DE) ...................... 10 2022 200 822.7

(51) Int. Cl.
| | |
|---|---|
| G02B 21/36 | (2006.01) |
| A61B 90/20 | (2016.01) |
| H04N 23/69 | (2023.01) |

(52) U.S. Cl.
CPC ............ *G02B 21/365* (2013.01); *A61B 90/20* (2016.02); *H04N 23/69* (2023.01); *A61B 2560/0233* (2013.01)

(58) Field of Classification Search
CPC .. G02B 21/365; G02B 21/0012; A61B 90/20; A61B 2560/0233; H04N 23/69;
(Continued)

(56) References Cited

U.S. PATENT DOCUMENTS

| | | | |
|---|---|---|---|
| 9,310,597 B2 | 4/2016 | Hein et al. | |
| 9,817,223 B2 | 11/2017 | Hein | |

(Continued)

FOREIGN PATENT DOCUMENTS

| | | |
|---|---|---|
| DE | 10 2012 024 737 | 6/2014 |
| DE | 10 2013 222 295 | 5/2015 |

(Continued)

*Primary Examiner* — Michael Lee
(74) *Attorney, Agent, or Firm* — NIXON PEABODY LLP; Jeffrey L. Costellia

(57) ABSTRACT

The invention relates to a method for adjusting and/or calibrating a medical microscope, the following being implemented for at least one observer beam path of the medical microscope: capturing respective image representations of an object at different magnification levels of a zoom optical unit, and determining a zoom center using the captured image representations as a starting point, and i) capturing respective further image representations at different axis positions of at least one linear or rotational movement axis of the medical microscope, a rotation of the capture device relative to the at least one linear or rotational movement axis being determined using the captured further image representations as a starting point, and/or ii) capturing respective further image representations of the object in different focal planes and/or at different working distances in the case of an off-centered imaging optical unit, a rotation of the capture device being determined using the captured further image representations as a starting point, and a reference marking being determined using the determined zoom center and the determined rotation as a starting point and being provided for adjustment and/or calibration purposes. Further, the invention relates to a medical microscope.

15 Claims, 10 Drawing Sheets

(58) Field of Classification Search
CPC .. H04N 13/204; H04N 13/246; H04N 13/296; H04N 17/002; H04N 23/60; H04N 23/695
See application file for complete search history.

(56) References Cited

U.S. PATENT DOCUMENTS

| | | | |
|---|---|---|---|
| 2014/0168762 A1 | 6/2014 | Hein et al. | |
| 2015/0346471 A1 | 12/2015 | Schwarz et al. | |
| 2016/0231552 A1 | 8/2016 | Hein | |
| 2018/0049840 A1* | 2/2018 | Awdeh | A61B 90/20 |
| 2019/0122026 A1* | 4/2019 | Acher | H04N 17/002 |
| 2019/0313902 A1* | 10/2019 | Charles | A61B 3/0025 |
| 2021/0112203 A1* | 4/2021 | Walden, II | H04N 23/695 |

FOREIGN PATENT DOCUMENTS

| | | | | |
|---|---|---|---|---|
| DE | 10 2014 210 099 | | 10/2015 | |
| EP | 3629071 A1 | * | 4/2020 | G02B 21/22 |

\* cited by examiner

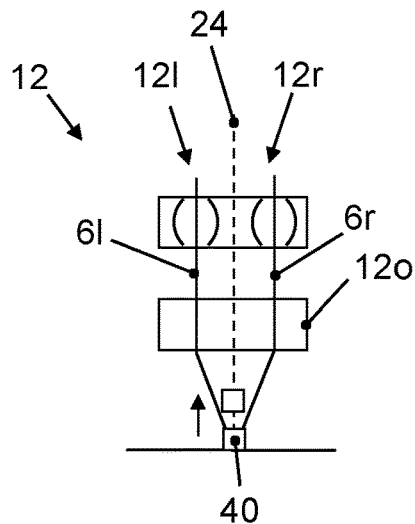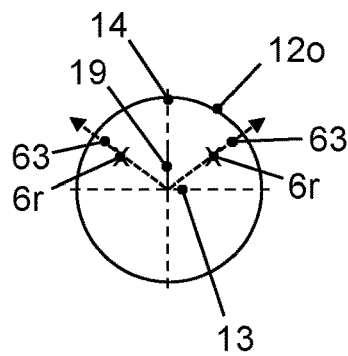
Fig. 10a      Fig. 10b
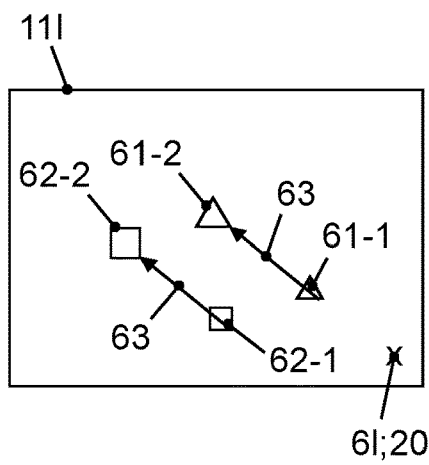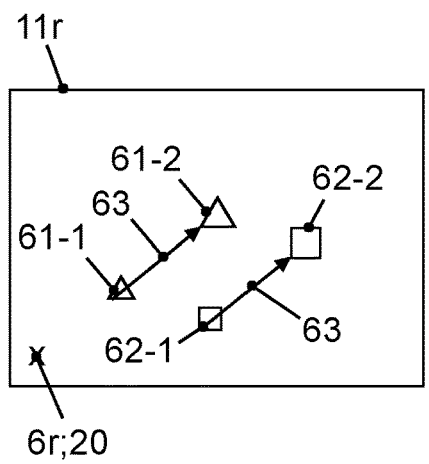
Fig. 10c      Fig. 10d
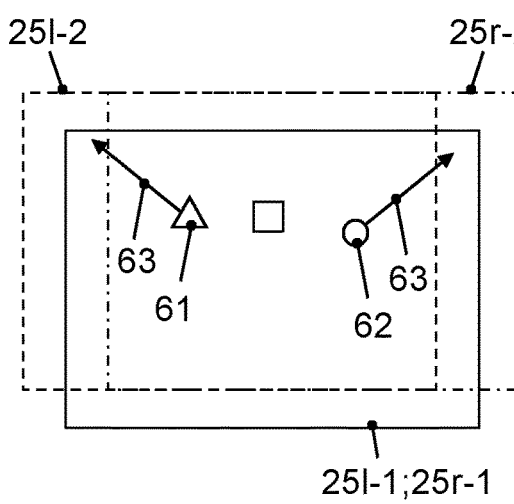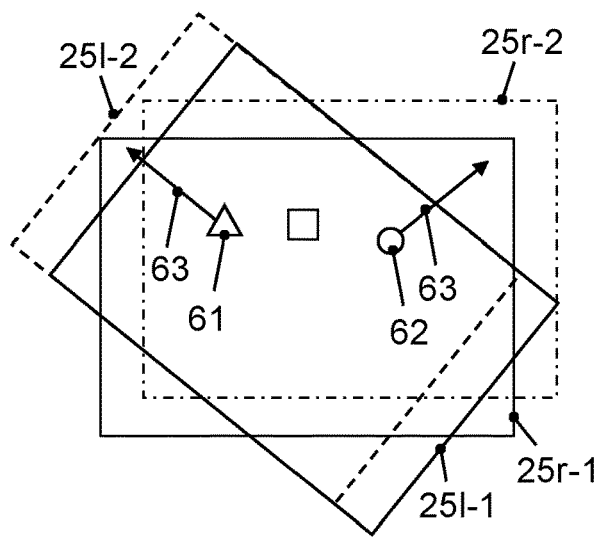
Fig. 10e      Fig. 10f

METHOD FOR ADJUSTING AND/OR CALIBRATING A MEDICAL MICROSCOPE AND MEDICAL MICROSCOPE

CROSS-REFERENCE TO RELATED APPLICATIONS

The present application claims priority under 35 U.S.C. § 119 to German Patent Application No. 102022200822.7, filed Jan. 25, 2022, the contents of which are incorporated by reference herein in their entirety.

The invention relates to a method for adjusting and/or calibrating a medical microscope and to a medical microscope.

So-called zero tubes are used for the adjustment of medical visualization systems, in particular of medical microscopes. These attempt to present the optical center of a main observer of the visualization system by way of a strict mechanical tolerance chain (optical unit to dovetail interface, on which the zero tube is assembled). The zero tube contains a graticule, in particular. Crosshairs representing the optical center are engraved thereon. Other components of the visualization system (camera, overlay device, autofocus laser, etc.) are adjusted in relation to this optical center. Following the adjustment, the information relating to a position and a rotation of the crosshairs is discarded as a result of the removal of the zero tube and can only be made available in the field by way of a service operation.

The invention is based on the object of improving, in particular simplifying, a method for adjusting and/or calibrating a medical microscope and a medical microscope.

According to the invention, the object is achieved by a method having the features of patent claim 1 and a medical microscope having the features of patent claim 15. Advantageous configurations of the invention are evident from the dependent claims.

Developing a reference marking for adjustment and/or calibration purposes by exploiting functions of the medical microscope so that an additional zero tube is no longer required is one of the basic concepts of the invention. To this end, an optical center of at least one observer beam path and a rotation of the observer beam path, in particular, are determined by way of a rotation of a capture device in the at least one observer beam path relative to linear or rotational movement axes and/or relative to axes of symmetry and/or planes of symmetry of an imaging optical unit of the medical microscope.

This is implemented by virtue of respective image representations of an object arranged in a capture region being captured by means of a capture device in the observation beam path at different magnification levels of a zoom optical unit in the observer beam path of the medical microscope in question. A zoom center is determined using the captured image representations as a starting point. In particular, the zoom center is the point in the captured image representations which does not move between the various magnification levels. In this case, the zoom center is considered to be the optical center of the observer beam path in particular.

Further, in an alternative, respective further image representations of the object are captured in different axis positions of at least one linear or rotational movement axis of the medical microscope which runs perpendicular to the optical axis of the observer beam path in question. A rotation, in particular a rotation angle or difference angle, of the capture device is determined relative to the at least one linear or rotational movement axis using the captured further image representations as a starting point. Ideally, that is to say in the case of a correct adjustment of the capture device relative to the at least one linear or rotational movement axis (in particular taking account of an optical image representation in the observer beam path), the object in the image representations would in each case be displaced along a target direction (e.g., along coordinate axes of an image sensor of the capture device) during the displacement along the linear or rotational movement axis. However, if the target direction does not run parallel to the linear movement axis of the medical microscope in question or perpendicular to the rotational movement axis of the medical microscope in question, then there is a rotation (in particular a rotation angle or difference angle) of the capture device vis-à-vis the linear or rotational movement axis, that is to say the target direction is rotated vis-à-vis the linear or rotational movement axis of the medical microscope in question or makes a difference angle with respect to the linear or rotational movement axis in question. The target direction arises, in particular, from an imaged direction of the extent of axis positions of the at least one linear or rotational movement axis in a captured image representation if an ideal adjustment and/or calibration of all components of the medical microscope is assumed. In the case of a rotational movement axis, the target direction extends perpendicular to the rotational movement axis in particular, on account of the rotation about the rotational movement axis. The target direction corresponds in particular to a direction of extent, imaged on an image sensor of the capture device via the observer beam path in question, of the at least one linear or rotational movement axis as the latter would run in an ideal model of the medical microscope. The rotation, in particular the rotation angle or difference angle, can be determined by a displacement along the at least one linear or rotational movement axis and by capturing further image representations at different axis positions.

Alternatively or additionally, provision is made in the case of an off-centered, in particular stereoscopic imaging optical unit of the medical microscope for respective further image representations of the object to be captured in different focal planes and/or at different working distances, with a rotation of the capture device of the imaging optical unit being determined using the captured further image representations as a starting point.

By way of example, in the case of a singly off-centered stereoscopic imaging optical unit of the medical microscope, provision is additionally or alternatively made for respective further image representations of the object to be captured in different focal planes in the case of a constant working distance, with a rotation of the capture device, in particular relative to a reference straight line and/or an axis of symmetry and/or a plane of symmetry of the stereoscopic imaging optical unit, being determined using the captured further image representations as a starting point. In this case, the axis of symmetry is defined in relation to a cross section through a main objective of the imaging optical unit in particular. A stereo angle of the stereoscopic imaging optical unit changes on account of the change in the focal plane. In this case, a magnification is preferably kept constant. In the case of different magnifications, the latter can in particular be removed by calculation and/or compensated for by means of image processing. The imaged object region changes as a result of the change in the stereo angle. In this case, the movement of the features of the object in the further image representations is, in particular and ideally and in the event of distortions being neglected or removed by calculation, along a straight line which in particular coincides with an axis of symmetry and/or a plane of symmetry of the stereoscopic imaging optical unit. In particular, this is the straight line along which the foci of the respective beam paths migrate toward or away from one another when the stereo angle is changed. By way of the movement of the features in the captured further image representations, it is possible to determine the direction of this straight line and, consequently, a direction of the reference straight line and/or of the axis of symmetry and/or plane of symmetry of the imaging optical unit. Subsequently, the rotation of the capture device can be determined using the reference straight line and/or axis of symmetry and/or plane of symmetry determined in this way as a starting point.

Further alternatively or additionally, in the case of a twofold off-centered stereoscopic imaging optical unit of the medical microscope for example, provision is made for respective further image representations of the object to be captured, in particular at a constant magnification, while the object is arranged at different distances from the imaging optical unit, with a rotation of the capture device, in particular relative to a reference straight line and/or an axis of symmetry and/or a plane of symmetry of the stereoscopic imaging optical unit, being determined using the captured further image representations as a starting point. If the object is moved in the direction of the imaging optical unit (especially in the z-direction if the capture region images an xy-plane) with otherwise constant settings, the features of the object move in the further image representations of the respective beam paths in one direction in each of the beam paths if distortion is neglected. These directions are determined for the two beam paths of the stereoscopic imaging optical unit, in each case on the basis of the features in the further image representations. In particular, these directions include an angle. Using this angle as a starting point, an angle bisector, for example, can be determined as a reference straight line (in particular in relation to the imaged object region) or an axis of symmetry (in particular in relation to a cross section of the main objective) and/or a plane of symmetry (in particular in relation to the imaging optical unit). Alternatively, a straight line perpendicular to the angle bisector can be used as a reference straight line or axis of symmetry and/or plane of symmetry. Subsequently, the rotation of the capture device can be determined using the reference straight line, axis of symmetry and/or plane of symmetry determined in this way as a starting point.

An imaging scale may change in the case of defocusing. Provision can be made for this to be modeled and/or removed by calculation. However, in particular, this need only be taken into account for those features not located on the axis of symmetry. Alternatively, it would also be possible to use only features in the vicinity of the axis of symmetry.

In principle, the determination of a reference straight line and/or axis of symmetry and/or plane of symmetry by virtue of varying a working distance is also possible in the case of a singly off-centered imaging optical unit. It is likewise possible, as a matter of principle, to capture further image representations in different focal planes even in the case of a twofold off-centered imaging optical unit. The procedure is analogous in each case. In principle, the variants may be combined in one embodiment.

Using the determined zoom center and the determined rotation, in particular the rotation angle or the difference angle, as a starting point, a reference marking (in particular in the shape of crosshairs which are overlaid into the observer beam path) is determined and provided for adjustment and/or calibration purposes.

In particular, a method for adjusting and/or calibrating a medical microscope is provided, the following being implemented for at least one observer beam path of the medical microscope: capturing respective image representations of an object at different magnification levels of a zoom optical unit in the at least one observer beam path by means of a capture device in the at least one observer beam path, and determining a zoom center using the captured image representations as a starting point, and i) capturing respective further image representations of the object, in particular at a constant magnification, at different axis positions of at least one linear or rotational movement axis of the medical microscope which in particular runs perpendicular to the optical axis of the at least one observer beam path, a rotation of the capture device relative to the at least one linear or rotational movement axis being determined using the captured further image representations as a starting point, and/or ii) capturing respective further image representations of the object in different focal planes and/or at different working distances in the case of an off-centered, in particular stereoscopic imaging optical unit of the medical microscope, a rotation of the capture device being determined using the captured further image representations as a starting point, and a reference marking being determined using the determined zoom center and the determined rotation as a starting point and being provided for adjustment and/or calibration purposes.

Further, a medical microscope, in particular, is developed, comprising: at least one observer beam path with a zoom optical unit, a capture device, and at least one linear or rotational movement axis, which in particular is arranged perpendicular to an optical axis of the at least one observer beam path, and/or an off-centered, in particular stereoscopic imaging optical unit; and a control device, with the control device being configured to determine a zoom center in the captured image representations, which each capture or have captured an object at different magnification levels of the zoom optical unit by means of the capture device; i) to determine a rotation of the capture device relative to the at least one linear or rotational movement axis using captured further image representations as a starting point, the said captured further image representations each capturing or having captured the object, in particular at a constant magnification, in different axis positions of the at least one linear or rotational movement axis of the medical microscope which in particular runs perpendicular to the optical axis of the at least one observer beam path; and/or ii) to determine a rotation of the capture device in the case of an off-centered, in particular stereoscopic imaging optical unit of the medical microscope using captured further image representations as a starting point, the said captured further image representations each capturing or having captured the object in different focal planes and/or at different working distances; and to determine a reference marking using the determined zoom center and the determined rotation as a starting point and to provide the said reference marking for adjustment and/or calibration purposes.

An advantage of the method and the medical microscope is that it is possible to create a reference marking at any time, and so a zero tube is no longer required for adjustment and/or calibration purposes. This allows adjustment and/or calibration of components in an observer beam path of the medical microscope during activation without an additional service operation, even following an initial adjustment and/or calibration. As a result, a visualization quality can be checked and kept constant.

The zoom center is determined, in particular, in relation to coordinates or coordinate axes of picture elements of an image sensor of the capture device in the at least one observer beam path and/or coordinates or coordinate axes of the captured image representations corresponding therewith. The rotation is likewise determined, in particular, in relation to the coordinates or coordinate axes of the picture elements of the image sensor in the at least one observer beam path and/or coordinates or coordinate axes of the captured further image representations corresponding therewith. However, other reference systems may also be chosen as a matter of principle.

A medical microscope is a surgical microscope in particular. However, a medical microscope may also be a microscope used for medical examinations and/or for diagnostic purposes, for example in the field of ophthalmology.

A common main objective of a stereoscopic imaging optical unit, which is jointly used by a right and a left beam path, has two axes of symmetry, especially in relation to the image representation or a cross section of the main objective, the said two axes of symmetry being perpendicular to one another and intersecting at the center of the main objective. In particular, the axes of symmetry of the cross section coincide with planes of symmetry of the imaging optical unit. In the case of a singly off-centered stereoscopic imaging optical unit, the respective optical axes of the right and the left beam path do not run through the center of the main objective but run through the main objective away from one of the axes of symmetry or planes of symmetry. In the case of a twofold off-centered stereoscopic imaging optical unit, the respective optical axes of the right and the left beam path do not run through the center of the main objective but run through the main objective away from both axes of symmetry or planes of symmetry.

Parts of the medical microscope, in particular the control device, can be designed, either individually or together, as a combination of hardware and software, for example as program code that is executed on a microcontroller or microprocessor. However, provision can also be made for parts to be designed as application-specific integrated circuits (ASICs) and/or field-programmable gate arrays (FPGAs), either on their own or in combination.

In an embodiment, provision is made for the provision to comprise a display of the reference marking on at least one display device of the medical microscope. This allows the reference marking to be captured visually and rendered usable during the adjustment and/or calibration. A display device can be both an external display device and a display device in the at least one observer beam path of the medical microscope. By way of example, the display device can be an overlay device which is able to overlay information and/or images into the observer beam path such that these can be presented next to and/or superimposed on a capture region captured by means of an imaging optical unit.

In an embodiment, provision is made for the determined reference marking to be displayed in the form of a virtual zero tube on the at least one display device of the medical microscope. As a result, an adjustment and/or calibration can be carried out in an already known manner, like in the case of a physical zero tube. In particular, such a virtual zero tube may comprise crosshairs, with the center of the crosshairs corresponding to the determined zoom center and one of the straight lines of the crosshairs running parallel to the at least one linear or rotational movement axis of the medical microscope.

In an embodiment, provision is made for the capture device to be adjusted and/or calibrated by means of the reference marking. In particular, provision is made for a rotation of the capture device relative to the at least one linear or rotational movement axis to be corrected by virtue of the capture device being rotated by the adjustment, in such a way that the determined rotation (in particular a rotation angle or difference value) vanishes. Alternatively or additionally, provision can be made for the determined rotation to be corrected by a calibration. This is implemented, in particular, by virtue of image representations captured by means of the capture device being appropriately rotated by means of (digital) image processing.

In an embodiment, provision is made for an overlay device in the at least one observer beam path to be adjusted and/or calibrated using the determined reference marking as a starting point. Since information overlaid into the at least one observer beam path by the overlay device is also captured by the capture device in the at least one observer beam path, a position and an alignment of the overlaid information can be compared to the determined reference marking. The overlay device can then be adjusted and/or calibrated using a comparison result as a starting point. By way of example, provision can be made for crosshairs to be overlaid by means of the overlay device and for these crosshairs to be compared to crosshairs of the reference marking. As a result of the comparison, both deviations of a relative position and of an alignment with respect to one another can be determined and used for adjustment and/or calibration purposes.

In an embodiment, provision is made for a reference object to be aligned with the determined reference marking, with components of the medical microscope being adjusted and/or calibrated on the basis of the aligned reference object. In this way, a physically present reference object can also be provided, with the aid of which it is possible to adjust and/or calibrate components of the at least one observer beam path. Additionally, the reference object can be aligned in the focus by way of a contrast evaluation of the image in this case. By way of example, the reference object may be aligned manually by virtue of the reference object being arranged in the capture region of the medical microscope and being positioned and aligned on the basis of the displayed reference marking, for example on the basis of the displayed virtual zero tube. Subsequently, it is possible to adjust and/or calibrate the components, including the capture device in the at least one observer beam path and/or a display device, for example an overlay device, on the basis of the positioned and aligned reference object. To this end, a user can detect the reference object and the (overlaid) reference marking through an eyepiece or by way of the display device of the medical microscope, with the reference marking being displayed in the at least one observer beam path by means of a display device, in particular an overlay device. Alternatively or additionally, use can also be made of an external display device, on which the capture region with the reference object and the reference marking are displayed. The reference marking can subsequently be redetermined and the implemented adjustment and/or calibration can be checked.

In an embodiment, provision is made for the determined reference marking to be stored, with a state of the medical microscope being monitored using the stored reference marking and at least one further reference marking determined at a later time as a starting point. This allows improved, in particular automated monitoring of a state of the medical microscope, in particular in view of a mechanical adjustment and/or calibration. By way of example, provision can be made for a reference marking captured at a later time to be compared with the stored reference marking. Deviations between the zoom centers and the rotations of the reference markings can then be determined and compared to respective threshold values. One of the thresholds being exceeded can be communicated to a user and/or a service technician, and/or a service signal or an adjustment signal can be generated in order to signal the need for a renewed adjustment and/or calibration and/or for a replacement of a component. By way of example, provision can be made for such a deviation to be checked automatically within the scope of the startup and/or shutdown of the medical microscope.

In an embodiment, provision is made for a respective reference marking to be determined for each capture device and/or each observer beam path of the medical microscope, with the capture devices and/or components in the observer beam paths being adjusted and/or calibrated relative to one another using the respectively determined reference markings as a starting point. In particular, this allows correction of a binocular aberration in the case of a stereo microscope with two observation beam paths, and so a three-dimensional image representation is improved.

In an embodiment, provision is made for the same features to be identified in the image representations captured for the different zoom levels and be assigned to one another in each case in order to determine the zoom center, with the zoom center being determined on the basis of an intersection of straight lines which arise by connecting the respective features corresponding to one another in the superimposed captured image representations. These measures, in particular a feature recognition required to this end, are carried out by means of the control device of the medical microscope. By way of example, methods of the computer vision and pattern recognition, known per se, can be used to this end. In the process, use can also be made of machine learning and artificial intelligence methods, known per se, in particular from the field of pattern recognition and feature extraction.

If a zoom center is determined for different zoom ranges (each comprising at least two zoom levels), then there ideally is no movement in the zoom center. A migration of the zoom center or a difference in position of determined zoom centers in different zoom ranges can be used to identify a low-quality and/or faulty optical unit. To this end, provision can be made for a respective zoom center to be determined for different zoom ranges, with positions of the determined zoom centers being compared to one another and with a difference in position between the zoom centers being compared with a specified threshold value. If the difference in position exceeds the specified threshold value, an (error) signal or an (error) notification is generated and provided, in particular output.

Further additionally or alternatively, provision can be made for the intersections of the straight lines for different zoom ranges (each comprising at least two zoom levels) to be compared with one another. A distribution of respective positions of the intersections can be used here as a measure for a quality criterion for assessing an optical unit and/or a state of the optical unit. To this end, provision can be made for a respective intersection of the straight lines to be determined in different zoom ranges, with positions of the determined intersections being compared to one another and with a difference in position between the intersections being compared with a specified threshold value. If a difference in position exceeds the specified threshold value, an (error) signal is generated and provided, in particular output.

In an embodiment, provision is made for the same features to be identified in the captured further image representations and assigned to one another in each case in order to determine the rotation, with a displacement direction of the same features being determined in relation to the superimposed captured further image representations using the same features as a starting point and with the rotation being determined using the determined displacement direction as a starting point. These measures, in particular a feature recognition required to this end, are carried out by means of the control device of the medical microscope. By way of example, methods of the computer vision and pattern recognition, known per se, can be used to this end. In the process, use can also be made of machine learning and artificial intelligence methods, known per se, in particular from the field of pattern recognition and feature extraction. By way of example, the rotation can then be determined by comparing the displacement direction with a target direction (e.g., a coordinate axis of the capture device).

In an embodiment, provision is made for an optical flow in the captured image representations to be evaluated in order to determine the zoom center. Then, the zoom center is the point in the captured image representations which does not move or moves the least. The measures required to this end are carried out by means of the control device of the medical microscope.

In an embodiment, provision is made for an optical flow in the captured further image representations to be evaluated in order to determine the rotation. In particular, a displacement direction, which is compared to a target direction, is determined using the optical flow as a starting point. Using a comparison result as a starting point, it is possible to determine the rotation, in particular a rotation angle or difference angle. The measures required to this end are carried out by means of the control device of the medical microscope.

In an embodiment, provision is made for the object to comprise a checkerboard and/or a ChArUco board. In this way, features that can be identified particularly easily can be provided on the object. This can improve a pattern recognition and position determination of the features in the captured image representations and captured further image representations.

In an embodiment, provision is made for the zoom center to be used as center for digital zoom. To this end, the reference marking is determined, stored and made available to a digital zoom function of a display device as a parameter value.

In an embodiment, provision is made for only a partial region of the captured further image representations in the vicinity of the zoom center to be used to determine the rotation. In particular, the partial region is a specified partial region. In particular, computational power required for evaluation purposes can be reduced as a result. Further, this may, in particular, also allow possibly present distortion effects to be reduced or avoided, which in particular reduce with distance from the zoom center.

Further features relating to the configuration of the medical microscope arise from the description of configurations of the method. Here, the advantages of the medical microscope are in each case the same as in the configurations of the method.

The invention is explained in greater detail below on the basis of preferred exemplary embodiments with reference to the figures. In the figures.

Figure 4A:
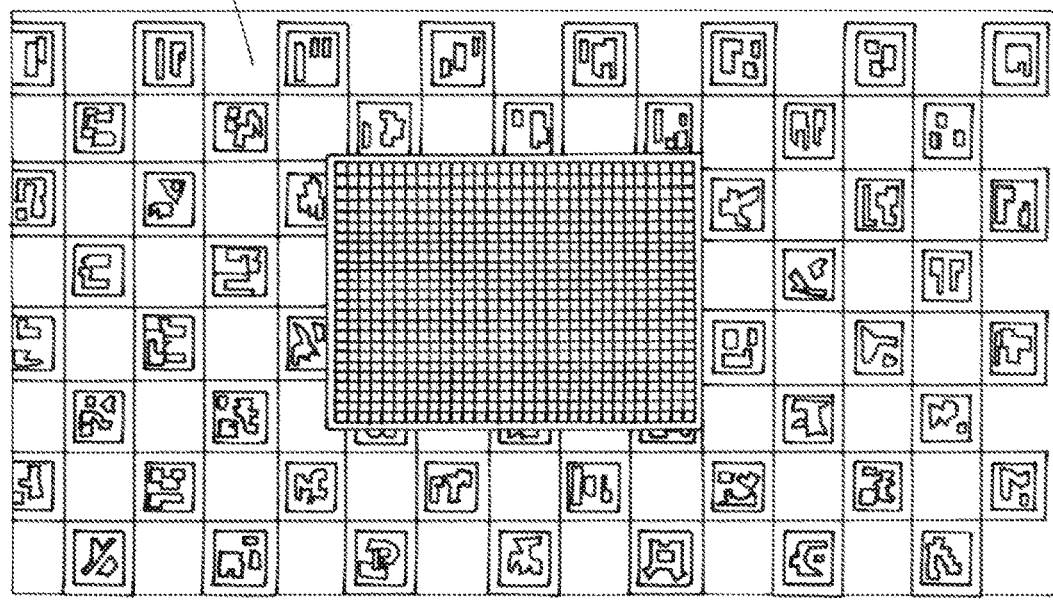
Figure 4B:
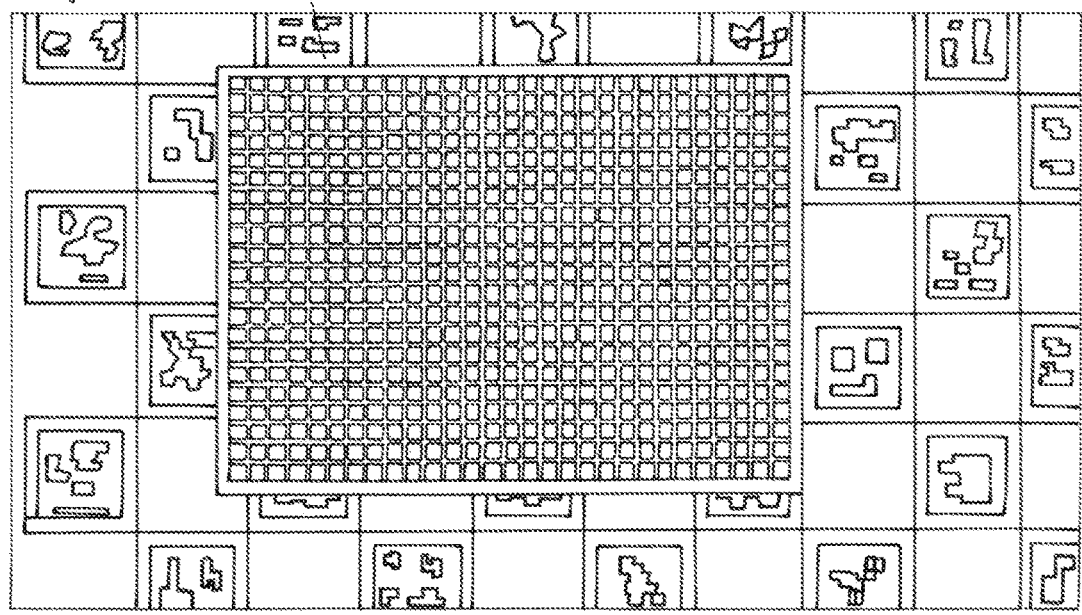
Figure 4C:
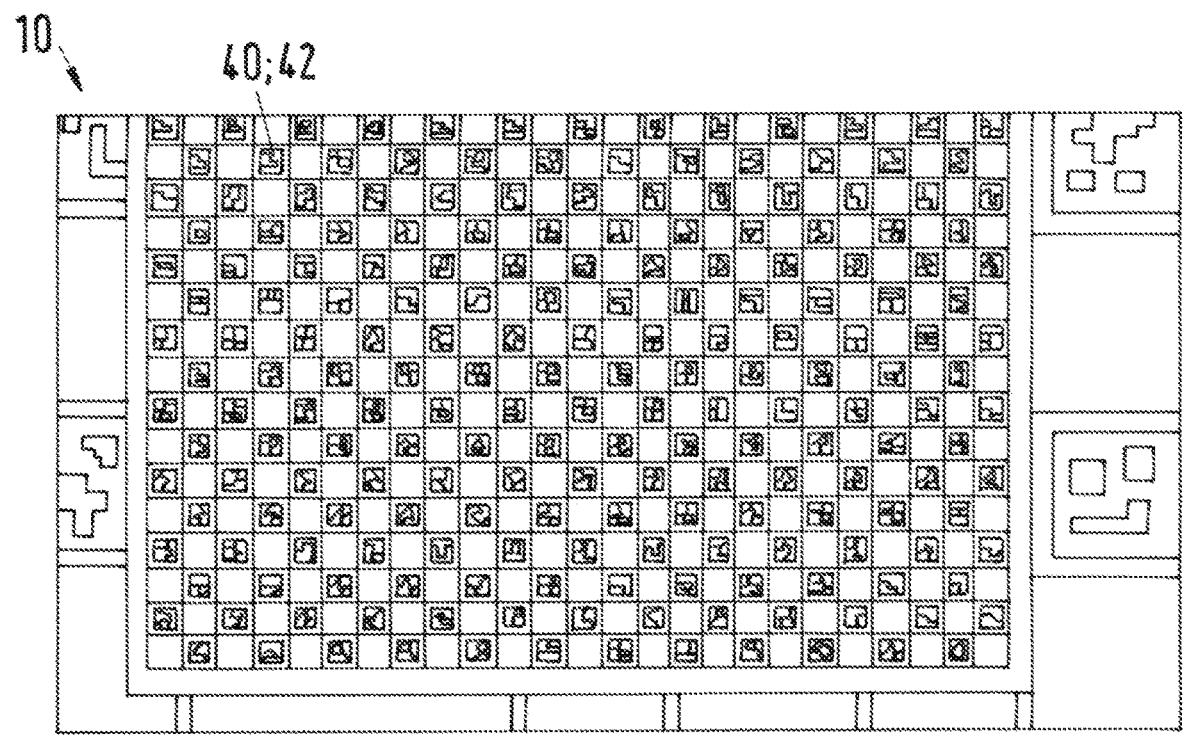
Figure 4D:
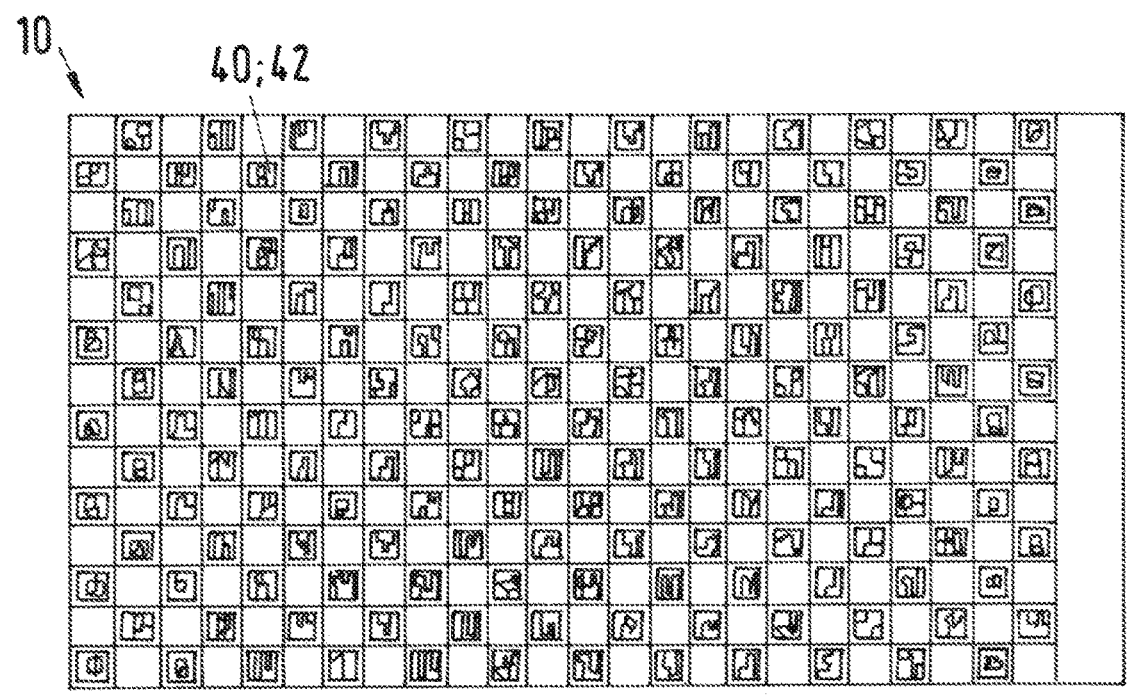
Figure 4E:
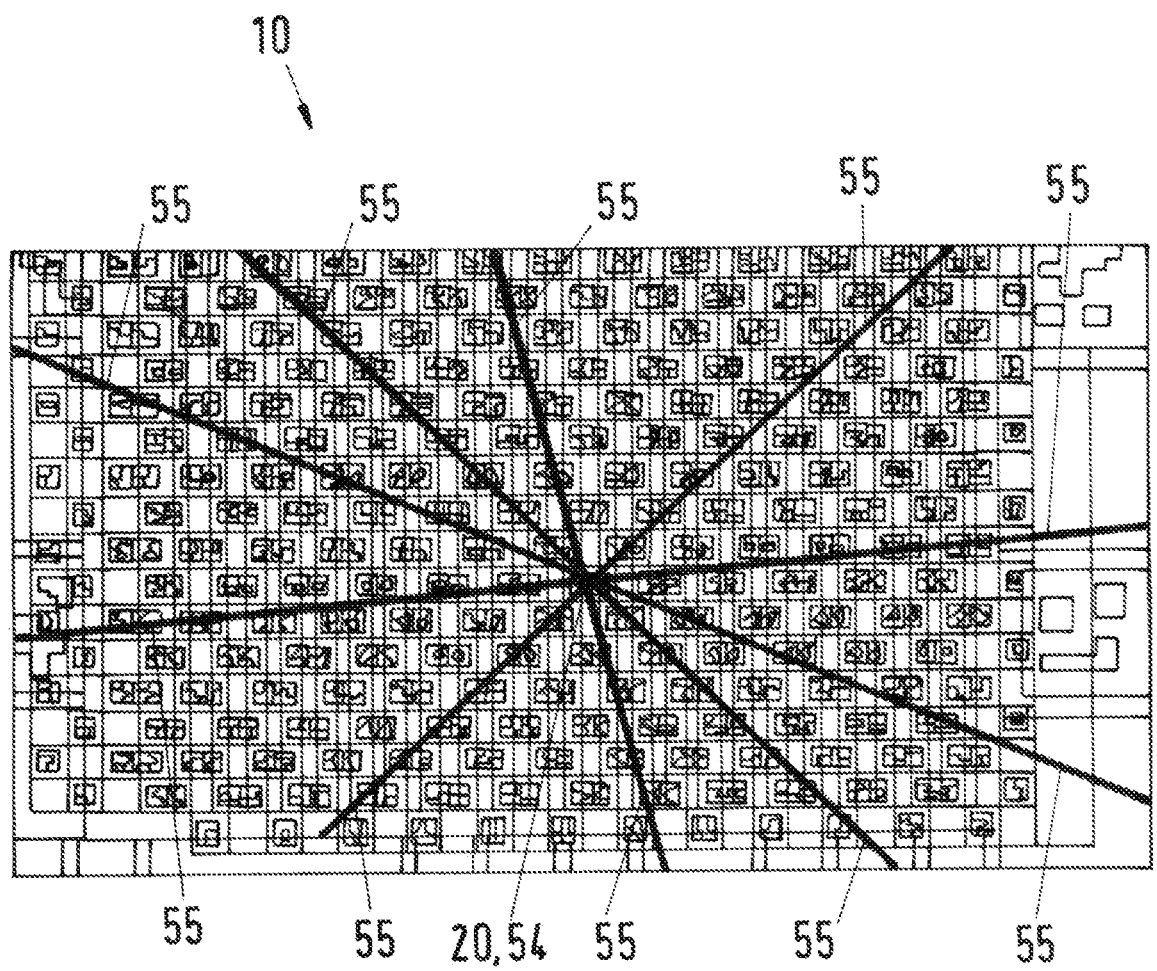
Figure 5:
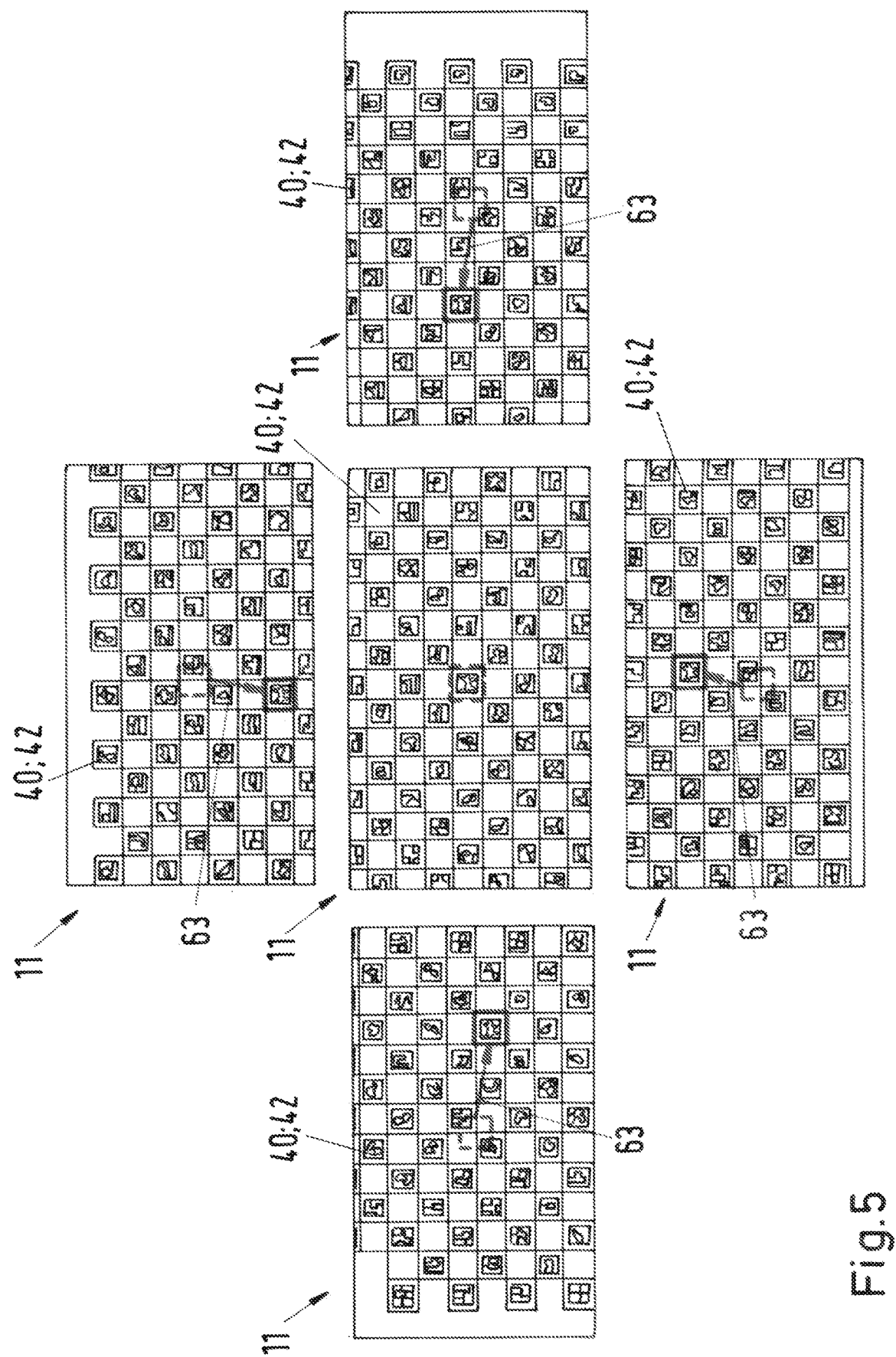
Figure 6:
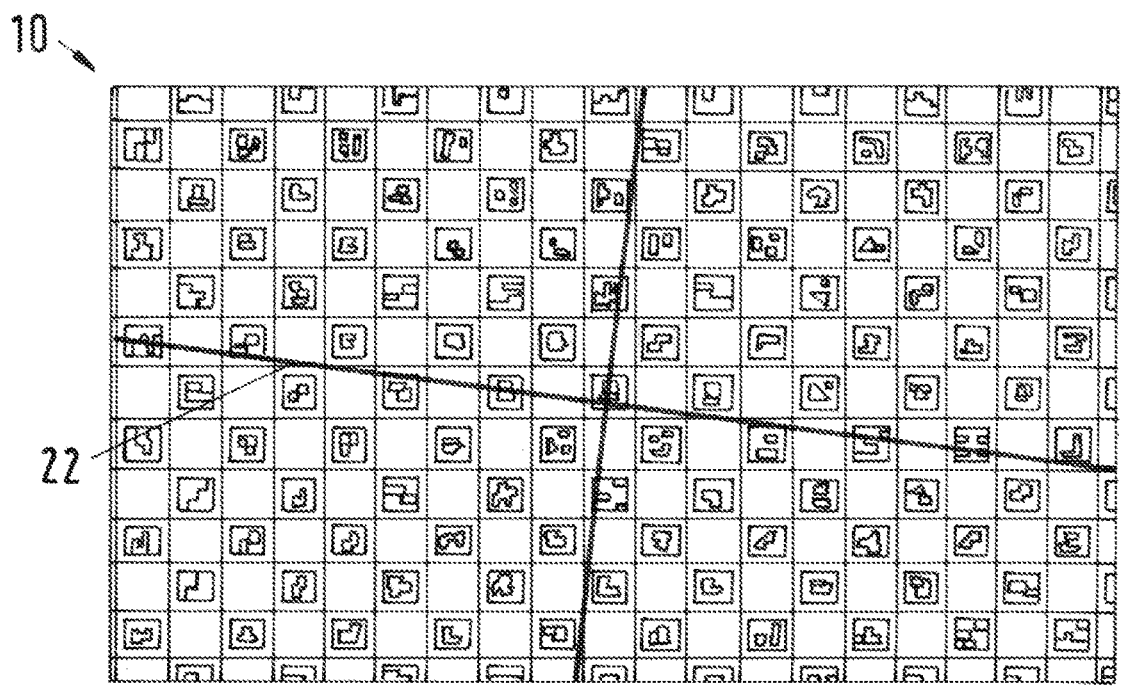
Figure 7:
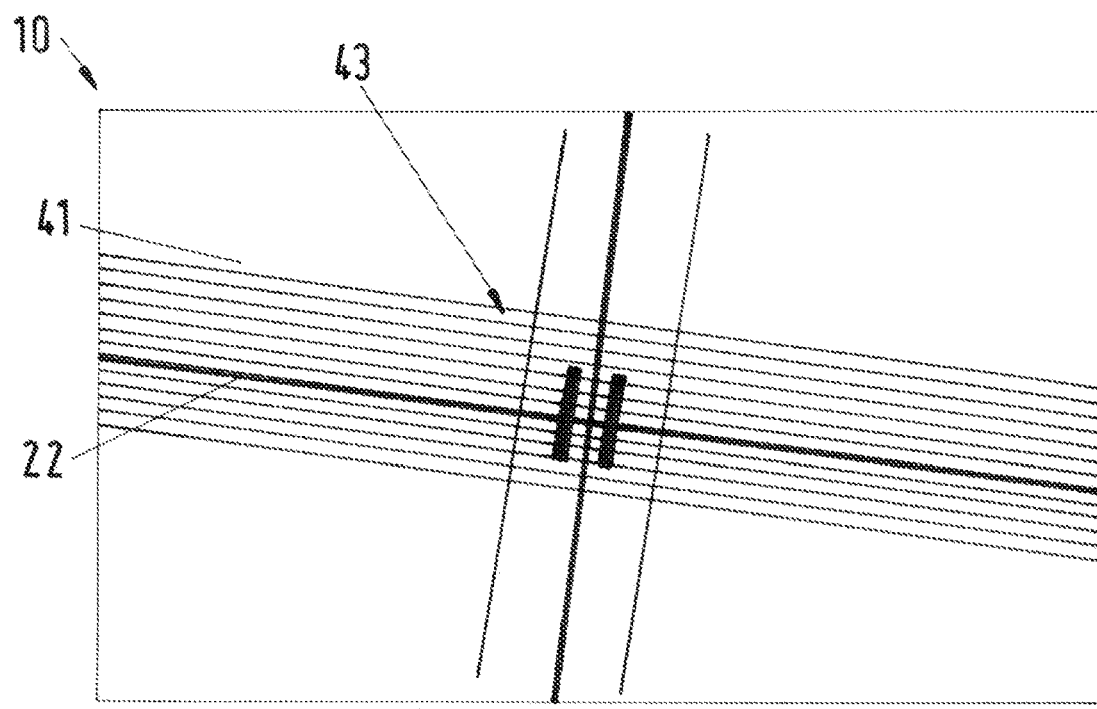
Figure 8:
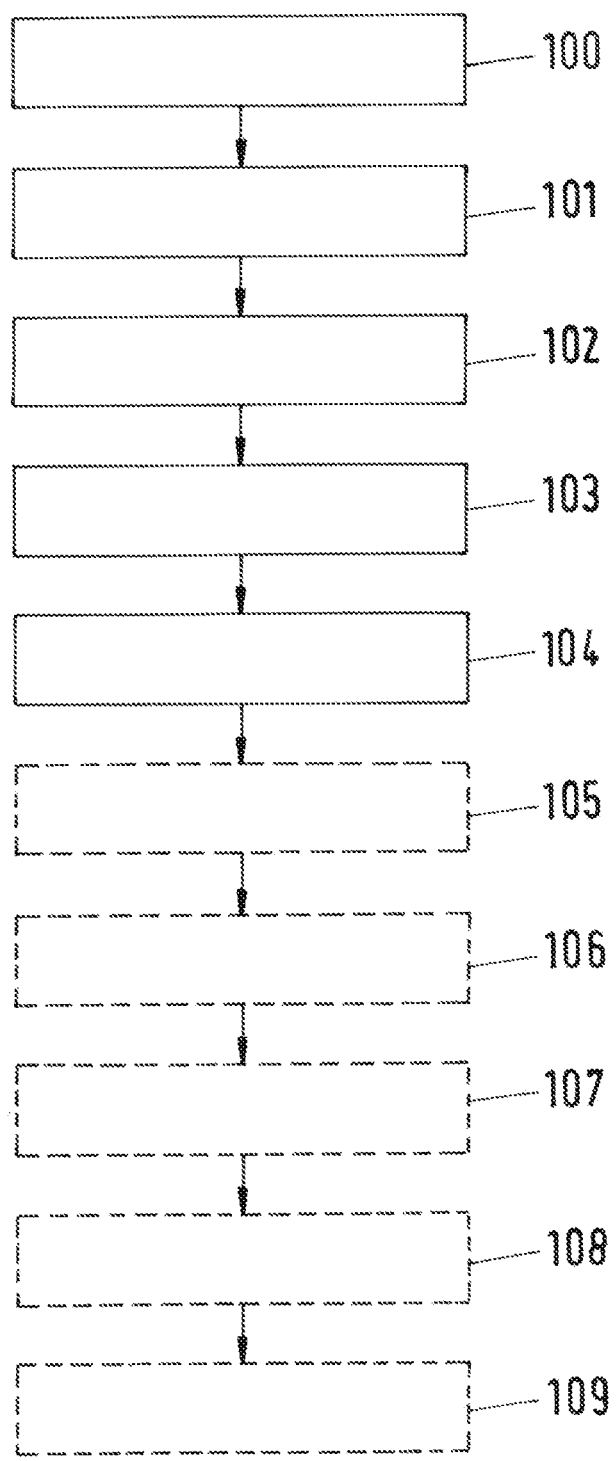

FIG. 4a-d show schematic representations of captured image representations of an object comprising a ChArUco board, at different magnification levels for elucidating an embodiment of the method and medical microscope;

FIG. 4e shows a schematic representation of superimposed captured image representations of different zoom levels for elucidating an embodiment of the method and medical microscope (determining the zoom center);

FIG. 5 shows a schematic representation of captured further image representations of an object comprising a ChArUco board, at different axis positions for elucidating an embodiment of the method and medical microscope (determining the rotation);

FIG. 6 shows a schematic representation of an image representation with a reference marking displayed therein, captured by means of a misaligned capture device, for elucidating an embodiment of the method and medical microscope;

FIG. 7 shows a schematic representation for elucidating a further embodiment of the method and medical microscope;

FIG. 8 shows a schematic flowchart of an embodiment of the method for adjusting the microscope;

FIG. 9a-9d show schematic representations for explaining a variant of the method and medical microscope;

FIG. 10a-10f show schematic representations for explaining a further variant of the method and medical microscope.

Figure 1:
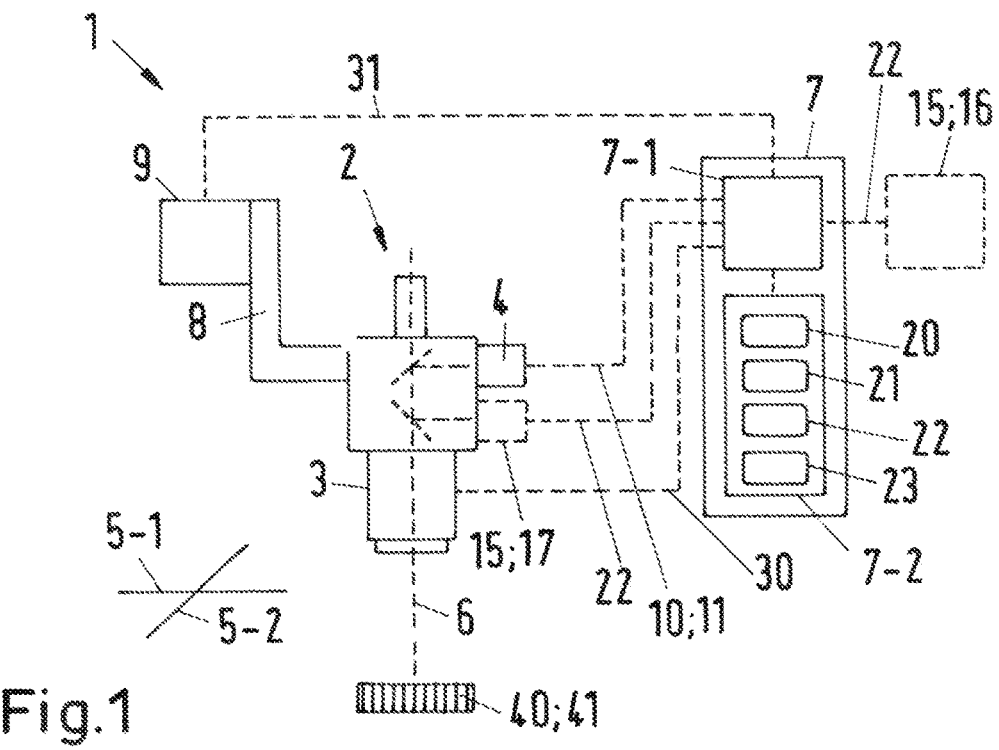
FIG. 1 shows a schematic representation of an embodiment of the medical microscope.

FIG. 1 shows a schematic representation of an embodiment of the medical microscope 1. The medical microscope 1 comprises an observer beam path 2 with a zoom optical unit 3, a capture device 4, for example a camera, and two linear or rotational movement axes 5-1, 5-2, which are arranged perpendicular to an optical axis 6 of the observer beam path 2. Only one observer beam path 2 has been shown for reasons of clarity; however, in principle, the medical microscope 1 may also comprise more than one observer beam path, in particular two observer beam paths. Further, the medical microscope 1 comprises a control device 7. By way of example, the control device 7 comprises a computing device 7-1, for example a microprocessor, and a memory 7-2. The method described in this disclosure is explained in more detail below on the basis of the medical microscope 1.

In particular, the medical microscope 1 furthermore comprises a stand 8, which is arranged in an actuator system 9. By way of the stand 8, the actuator system 9 is able to move the observer beam path 2 along the linear or rotational movement axes 5-1, 5-2.

The zoom optical unit 3, the capture device 4, and the actuator system 9 are subject to open-loop or closed-loop control by means of the control device 7.

The control device 7 is configured to determine a zoom center 20 in captured image representations 10, which each capture or have captured an object 40 at different magnification levels of the zoom optical unit 3 by means of the capture device 4. The various magnification levels are set at the zoom optical unit 3, in particular in automated fashion, by means of the control device 7, for the purposes of which the control device 7 generates control signals 30 and feeds these to the zoom optical unit 3. However, in principle, this may also be implemented manually or in any other way.

Further, in a variant, the control device 7 is configured to determine a rotation 21, in particular a rotation angle or difference angle, of the capture device 4 relative to the linear or rotational movement axis 5-1 using captured further image representations 11 as a starting point, the said captured further image representations each capturing or having captured the object 40, in particular at a constant magnification, at different axis positions of the linear or rotational movement axis 5-1 of the medical microscope that runs perpendicular to the optical axis 6 of the observer beam path 2. The various axis positions are set at the actuator system 9, in particular by means of the control device 7, for the purposes of which the control device 7 generates control signals 31 and feeds these to the actuator system 9.

In another variant, provision is alternatively or additionally made in the case of an off-centered, in particular stereoscopic imaging optical unit 12 of the medical microscope 1 for the control device 7 to be configured to determine a rotation 21 of the capture device 4 using captured further image representations 11 as a starting point, the said captured further image representations each capturing or having captured the object 40 in different focal planes F1, F2 (FIG. 9a) and/or at different working distances.

By way of example, provision is alternatively or additionally made in the case of a singly off-centered stereoscopic imaging optical unit of the medical microscope 1 for the control device 7 to be configured to determine a rotation 21 of the capture device(s) 4 relative to an axis of symmetry (in relation to a captured object region or a cross section through the main objective) and/or plane of symmetry (in relation to the imaging optical unit) of the stereoscopic imaging optical unit using captured further image representations 11 as a starting point, the said captured further image representations each capturing or having captured the object 40 at a constant magnification in various focal planes. This variant is explained schematically below on the basis of FIGS. 9a to 9d.

In a further example, provision is alternatively or additionally made in the case of a twofold off-centered stereoscopic imaging optical unit of the medical microscope 1 for the control device 7 to be configured to determine a rotation 21 of the capture device(s) 4 relative to an axis of symmetry and/or plane of symmetry of the stereoscopic imaging optical unit using captured further image representations 11 as a starting point, the said captured further image representations each capturing or having captured the object 40, in particular at a constant magnification, while the object 40 is arranged at different distances from the imaging optical unit 12. This variant is explained schematically below on the basis of FIGS. 10a to 10f.

The control device 7 subsequently determines a reference marking 22 using the determined zoom center 20 and the determined rotation 21 as a starting point, and provides the determined reference marking 22 for adjustment and/or calibration purposes.

A medical microscope 1 usually has several, in particular two linear or rotational movement axes 5-1, 5-2 which are arranged perpendicular to one another and perpendicular to the optical axis 6 of the observer beam path 2. The measures for determining the rotation 21 (in particular the rotation angle or difference angle) according to the first variant can then be carried out analogously for the further, in particular second, linear or rotational movement axis 5-2.

Provision can be made for the provision to comprise a display of the reference marking 22 on at least one display device 15 of the medical microscope 1. By way of example, the display device 15 can be a computer monitor 16. Further, provision can be made for the display device 15 to be an overlay device 17 of the medical microscope 1, by means of which information can be overlaid into the observer beam path 2 (in particular via a semi-transparent mirror) such that the said information can be captured both through an eyepiece and by a sensor of the capture device 4.

In particular, provision can be made for the determined reference marking 22 to be displayed in the form of a virtual zero tube on the at least one display device 15 of the medical microscope 1. Such a virtual zero tube comprises crosshairs in particular.

Provision can be made for the capture device 4 to be adjusted and/or calibrated by means of the reference marking 22. To this end, the determined reference marking 22, in particular a virtual zero tube in the form of crosshairs, can be displayed by means of the overlay device 17, for example, and overlaid into the observer beam path 2. Then, the capture device 4 is adjusted, in particular mechanically, such that an image center corresponds to the overlaid reference marking 22 and a profile of a two-dimensional grid of picture elements of the sensor of the capture device 4 corresponds to a profile of the straight line of the crosshairs. Subsequently, a reference marking 22 can be redetermined and the adjustment and/or calibration of the capture device 4 can be checked.

Further, provision can be made for the overlay device 17 in the observer beam path 2 to be adjusted and/or calibrated using the determined reference marking 22 as a starting point. To this end, the overlay device 17 is adjusted and/or calibrated in relation to the reference marking 22 in particular, in particular on the basis of a virtual zero tube in the form of crosshairs.

Provision can be made for a reference object 41 to be aligned with the determined reference marking 22, with components of the medical microscope 1 being adjusted and/or calibrated on the basis of the aligned reference object 41. In this case, components could be the zoom optical unit 3, the capture device 4, any other imaging optical unit, and/or the overlay device 17, for example.

Provision can be made for the determined reference marking 22 to be stored, with a state of the medical microscope 1 being monitored using the stored reference marking 22 and at least one further reference marking 23 determined at a later time as a starting point. To this end, in particular, a difference between the stored reference marking 22 and the further reference marking 23 captured at a later time is determined and, for example, compared to specified threshold values, for example for a difference in position and for a difference in rotation. Should one of the threshold values be exceeded, it is possible for example to generate a signal indicating a misalignment of the medical microscope 1. By way of example, the signal can be displayed on one of the display devices 15.

Provision can be made for the medical microscope 1 to have further observer beam paths (not shown here), each with a further capture device (not shown here). Provision can then be made for a respective reference marking 22 to be determined for each capture device and/or each observer beam path of the medical microscope 1, with the capture devices and/or components in the observer beam paths being adjusted and/or calibrated relative to one another using the respectively determined reference markings 22 as a starting point. By way of example, a binocular aberration in a stereomicroscope can be corrected in this way.

Provision can be made for only a partial region of the captured further image representations 11 in the vicinity of the zoom center 20 to be used to determine the rotation 21.

Figure 2:
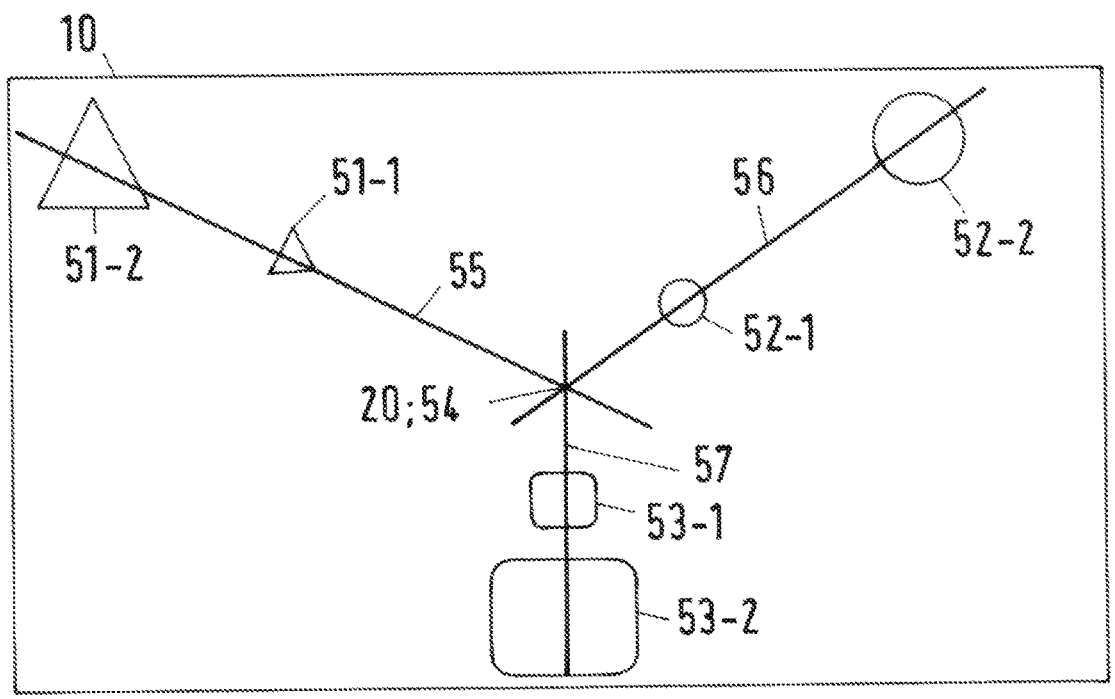
FIG. 2 shows a schematic representation for elucidating an embodiment of the method and medical microscope (determining the zoom center)

FIG. 2 shows a schematic representation for elucidating an embodiment of the method and medical microscope. In this embodiment, provision is made for the same features 51-$x$, 52-$x$, 53-$x$ to be identified in the image representations 10 captured for different zoom levels and be assigned to one another in each case in order to determine the zoom center 20, with the zoom center 20 being determined on the basis of an intersection 54 of straight lines 55, 56, 57 which arise by connecting the respective features 51-$x$, 52-$x$, 53-$x$ corresponding to one another in the superimposed captured image representations 10. Two image representations 10 with different zoom levels are superimposed in FIG. 2. When the magnification is increased, the features 51-$x$, 52-$x$, 53-$x$ migrate from the inside to the outside in the image representations 10 along the straight lines 55, 56, 57. The straight lines 55, 56, 57, the intersection 54 of which yields the zoom center 20, arise by connecting the features 51-$x$, 52-$x$, 53-$x$ that correspond to one another in each case. The zoom center 20 hardly moves, and ideally does not move at all, as a result of changes of the magnification in the various zoom levels. Computer vision and/or machine learning methods can be used when identifying and/or determining a position of the features 51-$x$, 52-$x$, 53-$x$.

Provision can be made for a respective zoom center 20 to be determined for different zoom ranges, with positions of the determined zoom centers 20 being compared to one another and with a difference in position between the zoom centers 20 being compared with a specified threshold value. If a difference in position exceeds the specified threshold value, an (error) signal is generated and provided, in particular output.

Further additionally or alternatively, provision can be made for the intersections 54 of the straight lines 55, 56, 57 for different zoom ranges (each comprising at least two zoom levels) to be compared with one another. A distribution of respective positions of the intersections 54 can be used here as a measure for a quality criterion for assessing an optical unit and/or a state of the optical unit. To this end, provision can be made for a respective intersection 54 of the straight lines 55, 56, 57 to be determined in different zoom ranges, with positions of the determined intersections 54 being compared to one another and with a difference in position between the intersections 54 being compared with a specified threshold value. If a difference in position exceeds the specified threshold value, an (error) signal or an (error) notification is generated and provided, in particular output.

Figure 3:
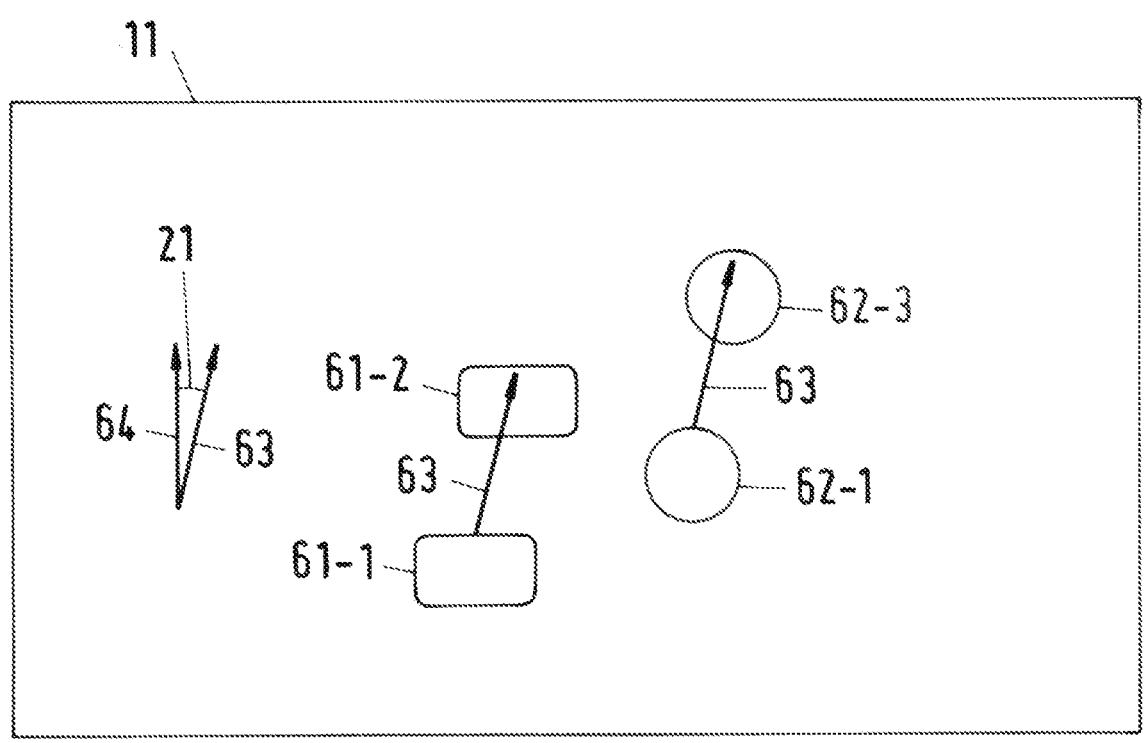
FIG. 3 shows a schematic representation for elucidating a further embodiment of the method and medical microscope (determining the rotation)

FIG. 3 shows a schematic representation for elucidating a further embodiment of the method and medical microscope. In this embodiment, provision is made for the same features 61-$x$, 62-$x$ to be identified in the captured further image representations 11 and be assigned to one another in each case in order to determine the rotation 21, in particular the rotation angle or difference angle, with a displacement direction 63 of the same features 61-$x$, 62-$x$ being determined in relation to the superimposed captured further image representations 11 using the same features 61-$x$, 62-$x$ as a starting point and with the rotation 21 being determined using the determined displacement direction 63 as a starting point. FIG. 3 shows two superimposed further image representations 11, which were captured with different axis positions of a linear or rotational movement axis. Since the linear axis or a direction perpendicular to the rotational axis does not run along the coordinate axis 64 of the picture elements of the image sensor of the capture device, which for example is defined as target orientation and/or target direction, the further image representations 11 are rotated vis-à-vis the linear movement axis or the direction perpendicular to the rotational movement axis, and this can be determined as rotation 21, in particular in the form of a rotation angle or difference angle, from the further image representations 11 (the rotation about the rotational axis in particular brings about a movement perpendicular to the rotational axis in the image representations 11). To this end, the displacement direction 63 is determined in each case by virtue of the same features 61-*x*, 62-*x* being interconnected in each case. A difference between a coordinate axis 64 of the image sensor and the displacement direction 63 yields the rotation 21 (in particular the rotation angle or difference angle).

In particular, provision can be made for the further image representations 11 to be captured and/or selected in such a way that as many identical features 61-*x*, 62-*x* as possible are present in the further image representations 11. Further, provision can be made for the further image representations 11 to be captured and/or selected in such a way that a distance between the identical features 61-*x*, 62-*x* is as large as possible in the further image representations 11. This can increase an accuracy when determining the rotation 21 (in particular of the rotation angle or difference angle). Computer vision and/or machine learning methods can be used when identifying and/or determining a position of the features 61-*x*, 62-*x*.

The measure is carried out analogously for a further linear or rotational movement axis which is perpendicular to the optical axis of the observer beam path. If a further, in particular second, linear or rotational movement axis is not perpendicular to a first linear or rotational movement axis, a value that has been averaged between the linear or rotational movement axes can be used for a target orientation and/or target direction.

Provision can be made for an optical flow in the captured image representations 10 to be evaluated in order to determine the zoom center 20. To this end, the point with the least movement in the various magnification levels is determined in the captured image representations 10. This point is then set as the zoom center 20.

Provision can be made for an optical flow in the captured further image representations 11 to be evaluated in order to determine the rotation 21, in particular a rotation angle or difference angle. The optical flow arises from the migration of features in the captured further image representations 11 when the observer beam path is moved along the linear or rotational movement axis. The rotation 21 (in particular the rotation angle or difference angle) can be determined in a manner analogous to FIG. 3 from a deviation between a movement direction determined from the optical flow and a target orientation and/or target direction.

Provision can be made for the object 42 to comprise a checkerboard and/or a ChArUco board 42 (FIGS. 4a to 4e). In this way, features that can be identified particularly easily can be provided.

A ChArUco board 42 is illustrated in FIGS. 4a to 4e in exemplary fashion. Shown is the determination of the zoom center 20, as has already been described with reference to FIG. 2. FIGS. 4a to 4d show image representations 10, which were captured for different magnification levels of the zoom optical unit. The image representations 10 shown in FIGS. 4c and 4d are superimposed in FIG. 4e. Straight lines 55, which intersect at an intersection 54, were laid through the same features (not provided with reference signs) in the two image representations 10. The intersection 54 is the zoom center 20.

FIG. 5 further shows the determination of a displacement direction 63 for determining the rotation with the aid of a ChArUco board 42. In this case, the observer beam path is displaced, in each case in both directions, along two linear or rotational movement axes arranged perpendicular to one another, with the further image representation 11 shown in the center of FIG. 5 being used as a starting point in each case. In this case, the further image representations 11 shown at the top and bottom of FIG. 5 correspond to a movement along/about one of the linear or rotational movement axes and the further image representations 11 shown to the left and right in FIG. 5 correspond in this case to a movement along/about the other one of the linear or rotational movement axes. In this case, the assumption is made that the linear or rotational movement axes are arranged perpendicular to one another and in each case perpendicular to the optical axis of the observer beam path, by means of which a capture device captures the further image representations 11. A movement about a rotational movement axis leads, in particular, to a movement perpendicular to the rotational movement axis in the captured image representations 11. The displacement direction 63 is elucidated on the basis of one of the ArUco IDs of the ChArUco board 42, the said ArUco ID being displaced in each case from the center of the further image representation 11 shown in the center of FIG. 5 to an edge region of the respectively following further image representation 11 (indicated by the respective arrows). The rotation (in particular a rotation angle or difference angle) is determined using the determined displacement direction 63 as a starting point, as already explained above with reference to FIG. 3, with the results for both linear or rotational movement axes being taken into account.

FIG. 6 shows a schematic representation of an image representation 10 with a reference marking 22 displayed therein, captured by means of a misaligned capture device, for elucidating an embodiment of the method and medical microscope. The reference marking 22 is displayed on a display device in this embodiment. In particular, provision is made for the determined reference marking 22 to be displayed jointly with a first captured image representation 10 on a display device 15 (FIG. 1). By way of example, provision can be made for the determined reference marking 22 to be overlaid into the observer beam path 2 (FIG. 1) by means of an overlay device 17, such that the said reference marking can be captured via an eyepiece and/or by means of the capture device 4. The reference marking 22 has the shape of crosshairs, with the intersection of the straight lines of the crosshairs corresponding to the zoom center. In the example shown, an orientation of the crosshairs corresponds to the rotation 21, in particular a rotation angle or difference angle, in each case between coordinate axes of a coordinate system of an image sensor of the capture device 4 and the linear or rotational movement axes 5-1, 5-2 (FIG. 1).

FIG. 7 shows a schematic representation for elucidating an embodiment of the method and medical microscope. The embodiment provides for a reference object 41 to be aligned with the determined reference marking 22, with components of the medical microscope being adjusted and/or calibrated on the basis of the aligned reference object 41. The reference object 41 shown in FIG. 7 has for example a plurality of line markings 43, which run parallel and perpendicular to one another. A profile of the line markings 43 is aligned manually on the basis of the reference marking 22, that is to say on the basis of the crosshairs. Following the alignment, the components of the medical microscope can be adjusted with the aid of the aligned reference object 41 (cf. FIG. 1 as well). The capture device can also be adjusted, with the capture device in the example shown having to be rotated through the determined rotation, in particular through the determined rotation angle or difference angle, in the clockwise direction to this end, so that a profile of coordinate axes of an image sensor of the capture device corresponds to the line markings 43 of the reference object 41.

FIG. 8 shows a schematic flowchart of an embodiment of the method for adjusting and/or calibrating a medical microscope. The method is explained below for one observer beam path of the medical microscope. However, the method steps can be carried out for further observation beam paths in the same way.

In a method step 100, respective image representations of an object are captured at different magnification levels of a zoom optical unit in the observer beam path by means of a capture device in the observer beam path.

In a method step 101, a zoom center is determined using the captured image representations as a starting point.

In a method step 102, respective further image representations of the object are captured, at a constant magnification, in different axis positions of at least one linear or rotational movement axis of the medical microscope which, in particular, runs perpendicular to the optical axis of the at least one observer beam path. In the process, further image representations are captured for at least two axis positions.

In a method step 103, a rotation, in particular a rotation angle or difference angle, of the capture device relative to the at least one linear or rotational movement axis, which may be defined as target orientation and/or target direction, is determined using the captured further image representations as a starting point.

Alternatively or additionally, respective further image representations of the object may be captured in different focal planes and/or for different working distances in method step 102 in the case of an off-centered imaging optical unit of the medical microscope, with a rotation of the capture device, in particular relative to an axis of symmetry (in relation to a cross section of the main objective) and/or a plane of symmetry (in relation to the imaging optical unit), of the optical unit being determined using the captured further image representations as a starting point. In this case, a rotation of the capture device, in particular relative to the axis of symmetry and/or plane of symmetry, of the stereoscopic imaging optical unit is determined in method step 103, using the captured further image representations as a starting point.

By way of example, alternatively or additionally, respective further image representations of the object, in particular at a constant magnification, may be captured in different focal planes in method step 102 in the case of a singly off-centered stereoscopic imaging optical unit of the medical microscope. In this case, a rotation of the capture device relative to an axis of symmetry and/or plane of symmetry of the stereoscopic imaging optical unit is determined in method step 103, using the captured further image representations as a starting point.

By way of example, further alternatively or additionally, respective further image representations of the object, in particular at a constant magnification, could be captured while the object is arranged at different distances from the imaging optical unit in method step 102 in the case of a twofold off-centered stereoscopic imaging optical unit of the medical microscope. In this case, a rotation of the capture device relative to an axis of symmetry and/or plane of symmetry of the stereoscopic imaging optical unit is determined in method step 103, using the captured further image representations as a starting point.

In a method step 104, a reference marking is determined using the determined zoom center and the determined rotation as a starting point and is provided for adjustment and/or calibration purposes. By way of example, the reference marking may comprise crosshairs.

In a method step 105, provision can be made for the provision to comprise a display of the reference marking on at least one display device of the medical microscope. In particular, provision can be made in this case for the determined reference marking to be displayed in the form of a virtual zero tube (e.g., in the form of crosshairs) on the at least one display device of the medical microscope.

In a method step 106, provision can be made for the capture device to be adjusted and/or calibrated by means of the reference marking.

Further, in a method step 107, provision can be made for an overlay device in the at least one observer beam path to be adjusted and/or calibrated using the determined reference marking as a starting point.

In a method step 108, provision can be made for a reference object to be aligned with the determined reference marking, with components of the medical microscope, in particular components in a respectively considered observer beam path, being adjusted and/or calibrated on the basis of the aligned reference object.

In a method step 109, provision can be made for the determined reference marking to be stored, with a state of the medical microscope being monitored using the stored reference marking and at least one further reference marking determined at a later time as a starting point. By way of example, this can be implemented by overlaying the stored reference marking in the observer beam path in question by means of an overlay device, with the overlay being captured by means of the capture device in the observer beam path and being compared with the further determined reference marking. Further, a check can be made as to whether the reference marking is still in the same position in the coordinate system of the image sensor at a later time. Using a comparison result as a starting point, it is then possible to cause a readjustment and/or a renewed calibration.

Further embodiments of the method have already been described with reference to FIGS. 1 to 7.

Figures 9A, 9B:
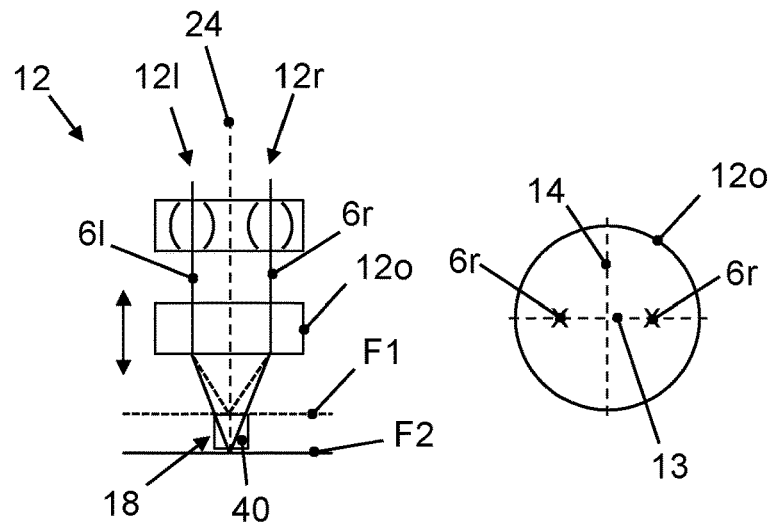
Figure 9C:
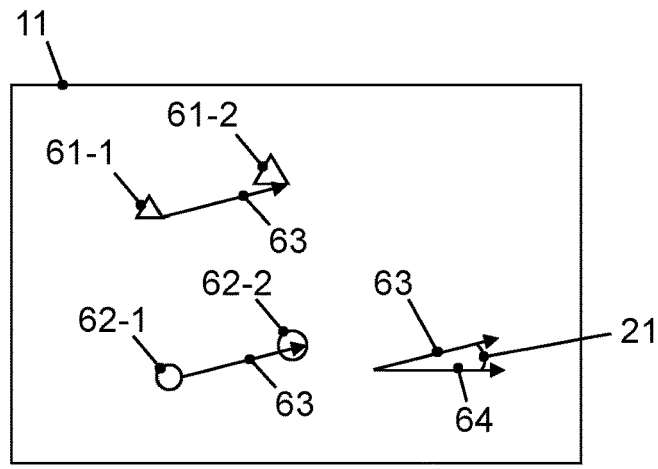

FIGS. 9a-9d show schematic representations for explaining a variant of the method and medical microscope. In the case of a singly off-centered stereoscopic imaging optical unit 12 of the medical microscope 1 (FIG. 1), provision is made for the control device 7 (FIG. 1) to be configured to determine a rotation 21 of the capture device 4 (FIG. 1) relative to an axis of symmetry 13 (in relation to a cross section through a main objective 12o) of the stereoscopic imaging optical unit 12 using captured further image representations 11 as a starting point, the said captured further image representations each capturing or having captured the object 40 at a constant magnification in various focal planes F1, F2. It is observed that the focal planes F1 and F2 for the two beam paths 12l, 12r in reality are tilted with respect to one another on account of the stereo angle or intersect at the stereo angle; however, this is neglected within the illustration for simplicity. FIG. 9a schematically shows the stereoscopic imaging optical unit 12. In the case of a change of the focal plane F1, F2, there is a change in a stereo angle between the left beam path 12l and the right beam path 12r. FIG. 9b schematically shows the image representation through the main objective 12o as a cross section. With reference to the cross section, there are two axes of symmetry 13, 14, which are perpendicular to one another and intersect in the center of the main objective 12o. The axis of symmetry 14 coincides with the plane of symmetry 24 of the main objective 12o illustrated in FIG. 9a. In the case of a singly off-centered stereoscopic imaging optical unit 12, as assumed here in exemplary fashion, the respective optical axes 6l, 6r of the left beam path 12l and the right beam path 12r do not run through the center of the main objective 12o but pass through the main objective 12o away from the axis of symmetry 14. However, the optical axes 6l, 6r are located on the axis of symmetry 13. FIG. 9c shows, in exemplary fashion, two captured further image representations 11 of the object 40 in two different focal planes F1, F2, the said captured further image representations being superimposed (in this case, captured further image representations 11 of only one of the beam paths 12l, 12r are sufficient). The same features 61-x, 62-x are displaced in relation to the picture elements which image these features 61-x, 62-x. It is therefore possible, in particular, to determine an optical flow in the form of a vector field of parallel vectors or a displacement direction 63. This displacement direction 63 coincides with the axis of symmetry 13 (or with the plane of symmetry corresponding therewith). The rotation 21 in the form of a deviation or difference angle can be determined between a coordinate axis 64 of the capture device 4 (or of an image sensor of the capture device 4), which specifies an actual orientation, and the displacement direction 64, as is indicated in FIG. 9c. Then, the orientation of the axis of symmetry 13 can subsequently be used as the target orientation or target direction, to which the coordinate axis 64 of the capture device 4 (or of the image sensor of the capture device 4) is adjusted (such that the target orientation and the coordinate axis 64 subsequently run at least parallel to one another).

Figure 9D:
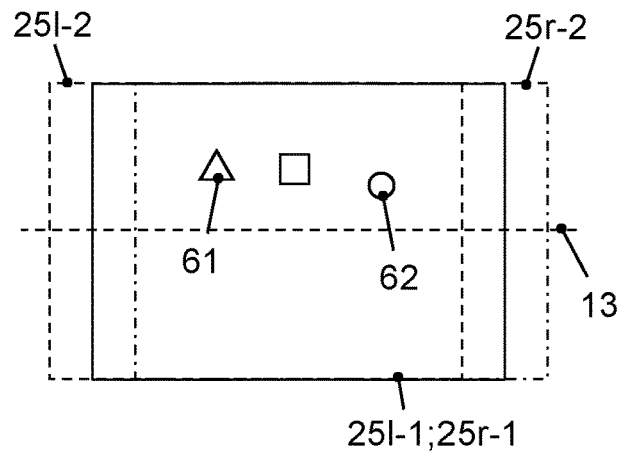

FIG. 9d shows a further schematic representation for explaining the variant with a singly off-centered stereoscopic imaging optical unit 12. Shown is a respective object region 25l, 25r, which is imaged and captured when a focus changes (labeled in each case by the suffix attached to the reference sign). If the focus of the main objective 12o changes, there is also a change in the respectively imaged object region 25l, 25r. In the focus, the object regions 25l-1, 25r-1 are superimposed, that is to say the left and the right optical image representation each image the same object region 25l-1, 25r-1. In the case of defocusing, the left beam path 12l and the right beam path 12r each image mutually offset object regions 25l-2, 25r-2. During defocusing, the features 61, 62 (by way of example, only two have been provided with a reference sign) move in a direction parallel to the axis of symmetry 13 in particular.

FIGS. 10a to 10f show schematic representations for explaining a further variant of the method and medical microscope. In the case of a twofold off-centered stereoscopic imaging optical unit 12 of the medical microscope 1 (FIG. 1), provision is made for the control device 7 (FIG. 1) to be configured to determine a rotation 21 of the capture device 4 (FIG. 1) relative to an axis of symmetry 13, 14 of the stereoscopic imaging optical unit 12 using captured further image representations 11 (or 11l, 11r) as a starting point, the said captured further image representations each capturing or having captured the object 40, at an in particular constant magnification, while the object 40 is arranged at different distances from the imaging optical unit 12. FIG. 10a schematically shows the stereoscopic imaging optical unit 12. By way of example, the object 40 is moved in the direction of the imaging optical unit 12 (or in particular parallel to the plane of symmetry 24 of the main objective), as indicated by the arrow, by means of a service hook (not shown) assembled below the microscope. In principle, the object 40 can also be moved in the opposite direction. FIG. 10b schematically shows the image representation through the main objective 12o as a cross section. With reference to the cross section of the main objective 12o, there are two axes of symmetry 13, 14, which are perpendicular to one another and intersect in the center of the main objective 12o. In the case of a twofold off-centered stereoscopic imaging optical unit 12, as assumed here in exemplary fashion, the respective optical axes 61, 6r of the left beam path 12l and the right beam path 12r do not run through the center of the main objective 12o but pass through the main objective 12o away from both axes of symmetry 13, 14. In exemplary fashion, FIG. 10c shows two superimposed left further image representations 11l, which were captured through the left beam path 12l for different object positions. In exemplary fashion, FIG. 10d shows two superimposed right further image representations 11r, which were captured accordingly through the right beam path 12r for the different object positions. In the focus, the respective optical axis 61, 6r (or the determined zoom center 20) always strikes the same object point, and so the latter is at rest in the image representations 11l, 11r, that is to say one object point is always imaged on the same picture elements of the capture device.

Should the object be moved in the direction of the imaging optical unit 12 (or in particular parallel to the plane of symmetry 24 of the main objective 24) with otherwise constant settings, a feature 61-x, 62-x of the object 40 moves in a certain direction in both beam paths 12l, 12r in the case of a reducing distance between object 40 and imaging optical unit 12. These directions are determined for both beam paths 12l, 12r of the stereoscopic imaging optical unit 12. Using these directions as a starting point, it is possible for example to determine an angle bisector 19 (FIG. 10b) as an axis of symmetry 14. Alternatively, a direction perpendicular to the angle bisector 19 in the object region can be used as axis of symmetry 13. Subsequently, the rotation 21 of the capture device(s) 4 can be determined using as a starting point the axis of symmetry 13, 14 determined thus, for example by virtue of comparing a coordinate axis of the capture device 4 (or of an image sensor of the capture device 4) with the axis of symmetry 13, 14 and, in particular, determining a difference angle as rotation 21. The axis of symmetry 13, 14 determined thus subsequently serves as target direction in particular, with respect to which the coordinate axis of the capture device 4 (or of an image sensor of the capture device 4) can be adjusted.

FIGS. 10e and 10f show further schematic representations for explaining the further variant with a twofold off-centered stereoscopic imaging optical unit 12. An object region 25l, 25r imaged by a left beam path 12l and a right beam path 12r of the imaging optical unit 12 changes in the case of a change of the working distance. This is shown schematically in FIG. 10e for two working distances, which are each labeled by the suffix attached to the reference sign. In this case, a first working distance (suffix 1) corresponds to focusing in particular and, in this case, a second working distance (suffix 2) corresponds to defocusing in particular. In this case, the displacement directions 63 of features 61, 62, labeled in exemplary fashion, are also depicted, the said displacement directions arising from the change in the working distance. In this case, the displacement directions 63 are determined in particular in relation to a feature arrangement that is identical in both object regions 25l, 25r (pattern recognition methods known per se can be used for the identification of the features). Using the determined displacement directions 63 as a starting point, it is then possible for example to determine an angle and an angle bisector 19 (FIG. 10b), as already described above. FIG. 10f shows the situation in the case of captured object regions 25l, 25r that are twisted relative to one another (that is to say, the rotations of the capture devices are different in particular). In this case, too, the displacement directions 63, an angle between the displacement directions 63, and an angle bisector 19 can be determined in the object region, in particular on account of the same feature arrangement in the two object regions 25*l*, 25*r*. Subsequently, the capture devices can be adjusted in order to correct the respective rotation.

The embodiments have been explained in exemplary fashion on the basis of a stereoscopic imaging optical unit. In principle, however, the method can be applied completely analogously to a monoscopic imaging optical unit or to an individual beam path. In this case, provision can be made in particular for a reference direction or target direction to be defined as a reference marking using a displacement direction 63 determined by a change in the focal plane and/or in the case of different working distances as a starting point, a coordinate axis of the capture device 4 (or of the image sensor of the capture device 4) being able to be adjusted in relation to the said reference direction or target direction.

LIST OF REFERENCE SIGNS

1 Medical microscope
2 Observer beam path
3 Zoom optical unit
4 Capture device
5-1 Linear or rotational movement axis
5-2 Linear or rotational movement axis
6 Optical axis
6*l* Optical axis (left beam path)
6*r* Optical axis (right beam path)
7 Control device
7-1 Computing device
7-2 Memory
8 Stand
9 Actuator system
10 Captured image representation
11 Captured further image representation
12 Stereoscopic imaging optical unit
12*l* Left beam path
12*r* Right beam path
12*o* Main objective
13 Axis of symmetry
14 Axis of symmetry
15 Display device
16 Computer monitor
17 Overlay device
18 Stereo angle
19 Angle bisector
20 Zoom center
21 Rotation
22 Reference marking
23 Further reference marking
24 Plane of symmetry
25*l* Object region (left beam path)
25*r* Object region (right beam path)
30 Control signals
31 Control signals
40 Object
41 Reference object
42 ChArUco board
43 Line markings
51-*x* Feature
52-*x* Feature
53-*x* Feature
54 Intersection
55 Straight line
56 Straight line
57 Straight line
61-*x* Feature
62-*x* Feature
63 Displacement direction
64 Coordinate axis of the image sensor (target orientation)
100-109 Method steps of the method
F1, F2 Focal plane

The invention claimed is:

1. A method for adjusting and/or calibrating a medical microscope, the following being implemented for at least one observer beam path of the medical microscope:
capturing respective image representations of an object at different magnification levels of a zoom optical unit in the at least one observer beam path by means of a capture device in the at least one observer beam path, and
determining a zoom center using the captured image representations as a starting point, and
i) capturing respective further image representations of the object at different axis positions of at least one linear or rotational movement axis of the medical microscope, a rotation of the capture device relative to the at least one linear or rotational movement axis being determined using the captured further image representations as a starting point, and/or
ii) capturing respective further image representations of the object in different focal planes and/or at different working distances in the case of an off-centered imaging optical unit of the medical microscope, a rotation of the capture device being determined using the captured further image representations as a starting point, and
determining a reference marking using the determined zoom center and the determined rotation as a starting point and being provided for adjustment and/or calibration purposes.

2. The method as claimed in claim 1, wherein the determined reference mark being provided comprises displaying the reference marking on at least one display device of the medical microscope.

3. The method as claimed in claim 2, wherein the displaying the determined reference marking is in the form of a virtual zero tube on the at least one display device of the medical microscope.

4. The method as claimed in claim 1, further comprising adjusting and/or calibrating the capture device based on the reference marking.

5. The method as claimed in claim 1, further comprising adjusting and/or calibrating an overlay device in the at least one observer beam path based on the determined reference marking as a starting point.

6. The method as claimed in claim 1, further comprising aligning a reference object with the determined reference marking, and adjusting and/or calibrating components of the medical microscope based on the aligned reference object.

7. The method as claimed in claim 1, further comprising storing the determined reference marking, and monitoring a state of the medical microscope using the stored reference marking and at least one further reference marking determined at a later time as a starting point.

8. The method as claimed in claim 1, further comprising determining a respective reference marking for each capture device and/or each observer beam path of the medical microscope, and adjusting and/or calibrating each capture device and/or components in the observer beam paths relative to one another using the respectively determined reference markings as a starting point.

9. The method as claimed in claim 1, further comprising identifying same features in the image representations captured for different zoom levels, and assigning the same features to one another in each case in order to determine the zoom center, with the zoom center being determined on the basis of an intersection of straight lines which arise by connecting the respective features corresponding to one another in the superimposed captured image representations.

10. The method as claimed in claim 1, further comprising identifying same features in the captured further image representations, and assigning the same features to one another in each case in order to determine the rotation, with a displacement direction of the same features being determined in relation to the superimposed captured further image representations using the same features as a starting point and with the rotation being determined using the determined displacement direction as a starting point.

11. The method as claimed in claim 1, further comprising evaluating an optical flow in the captured image representations to determine the zoom center.

12. The method as claimed in claim 1, further comprising evaluating an optical flow in the captured further image representations to determine the rotation.

13. The method as claimed in claim 1, wherein the object comprises a checkerboard and/or a ChArUco board.

14. The method as claimed in claim 1, wherein only a partial region of the captured further image representations in the vicinity of the zoom center is used to determine the rotation.

15. A medical microscope, comprising:
at least one observer beam path with
a zoom optical unit,
a capture device, and
at least one linear or rotational movement axis and/or an off-centered imaging optical unit; and
a control device,
with the control device being configured
to determine a zoom center in captured image representations, which each capture or have captured an object at different magnification levels of the zoom optical unit by means of the capture device;
  i) to determine a rotation of the capture device relative to the at least one linear or rotational movement axis using captured further image representations as a starting point, the said captured further image representations each capturing or having captured the object in different axis positions of the at least one linear or rotational movement axis of the medical microscope; and/or
  ii) to determine a rotation of the capture device in the case of the off-centered imaging optical unit of the medical microscope using captured further image representations as a starting point, the said captured further image representations each capturing or having captured the object in different focal planes and/or at different working distances, and
to determine a reference marking using the determined zoom center and the determined rotation as a starting point and to provide the said reference marking for adjustment and/or calibration purposes.

* * * * *